United States Patent [19]

Flynn

[11] Patent Number: 4,572,175

[45] Date of Patent: Feb. 25, 1986

[54] MULTI-MODE DEMAND VALVE

[76] Inventor: Stephen D. Flynn, 255 Chartwell Rd., Oakville, Ontario, Canada

[21] Appl. No.: 515,621

[22] Filed: Jul. 20, 1983

[51] Int. Cl.$^4$ .......................................... A01M 16/00
[52] U.S. Cl. .......................... 128/203.11; 128/204.26; 128/205.13; 128/205.24
[58] Field of Search ........... 128/202.8, 203.11, 205.13, 128/204.26, 204.28, 205.24; 137/493.8, 494

[56] References Cited

U.S. PATENT DOCUMENTS

| | | | |
|---|---|---|---|
| 2,598,525 | 5/1952 | Fox | 128/205.13 |
| 3,249,107 | 5/1966 | Delest | 128/204.28 |
| 3,474,785 | 10/1969 | Jansson | 128/204.28 |
| 3,795,257 | 3/1974 | Fabish et al. | 137/491 |
| 3,895,626 | 7/1975 | Elfstrand | 128/205.24 |
| 4,249,528 | 2/1981 | Mathes | 128/205.24 |
| 4,411,285 | 10/1983 | Oswell | 128/204.26 |

Primary Examiner—Henry J. Recla
Assistant Examiner—Karin M. Reichle
Attorney, Agent, or Firm—George A. Rolston

[57] ABSTRACT

A multi-function valve for administration of gases having a valve chamber with an administration opening for delivery of gases to a patient, a pressurized gas inlet, an inlet valve with an arm extending into the interior of the chamber, a resuscitation fluid inlet opening into such chamber, a diaphragm dividing the chamber into two halves with the resuscitation inlet on one side and the administration opening and the pressurized gas inlet on the opposite side, the diaphragm having a contact portion movable into and out of contact with the arm, and an opening in the diaphragm for fluid flow from one side of the chamber to the other, the opening being sized to permit the diaphragm to respond to fluid flow in the chamber, and cause operation of the gas inlet valve.

12 Claims, 4 Drawing Figures

MULTI-MODE DEMAND VALVE

The invention relates to devices for the administration of gases, and in particular to a gas administration valve having a multi-purpose function.

BACKGROUND OF THE INVENTION

Administration of gases and gas mixtures to patients may be required in a variety of circumstances. Where a patient has ceased breathing, or is breathing with difficulty and requires assistance, some form of resuscitation treatment by a medical assistant may be required. This may take the form of the administration of a gas mixture with or without manual assistance, or with or without a form of mouth-to-mouth resuscitation, depending upon the condition of the patient and the circumstances, and even upon the equipment available and the location. In addition, the type of resuscitation effort applied may depend upon the age of the patient. For example, infants require a more gentle form of treatment than can be applied to adults.

Another circumstance where gas administration may be required, is for analgesic purposes or for anaesthetic purposes. Where, for example, a patient is in pain, due, for example, to an injury or an accident, gas mixtures may be administered for the relief of pain. Where such a patient is involved in an accident, and is, for example, pinned by some structure or article, such gas mixtures may have to be self-administered in order to produce temporary unconsciousness so as to enable rescue workers to free the victim.

In other circumstances, a victim may be suffering from partial disability due to inhalation of noxious gases, and may simply require self-administered gas mixtures for breathing purposes in order to overcome the effects of the incident.

These are merely examples of various different situations in which the administration of gases may be required. It will be appreciated that such gases may be administered in different ways, other than those suggested herein. In addition, reference to administration of "gases" is deemed to include any gas or mixture of gases which may be administered for breathing purposes, or for any treatment of any condition, or for relief of pain, or for anaesthetic purposes, and includes the administration of fresh air.

Different problems occur when gases are administered in such a wide variety of circumstances.

For example, mouth-to-mouth resuscitation is known to produce possible undesirable results. Where direct mouth-to-mouth resuscitation is applied, simply by placing the mouth over the mouth of the patient, it is possible for the medical assistant to receive infection from the patient. Instances are well known, where, for example, paramedical personnel have become infected as a result of giving emergency mouth-to-mouth resuscitation.

In an attempt to overcome this problem, it is well known to provide some form of mouth piece and mask, by means of which mouth-to-mouth resuscitation may be given through a mask and tube. Even in this case, however, it is possible for the assistant to receive exhaled breath from the patient.

A further and more fundamental disadvantage is the fact that the medical assistant will be administering his own exhaled air. Normally, exhaled air contains approximately 15% free oxygen. This percentage is, of course, reduced in relation to normal fresh air and is generally speaking not sufficient to support life over a continuous period.

It is, therefore, highly desirable to supply some form of gas mixture or oxygen supplement when applying resuscitation.

A wide variety of different systems are available on the market for resuscitation by administering oxygen or mixtures of air and oxygen, through various forms of masks' valves and bellows-type devices or bags.

These systems do, however, involve a certain cash investment, and are often not available at the scene of the emergency. In addition, however, they do require a certain degree of training in their use. Operators of such equipment require to develop a sensitive "feel" on the pressure in the bellows or bag, so as to avoid overpressuring the lungs of the patient. If the airway is obstructed, then it is dangerous to overpressure the bag since it will increase the obstruction, and operators must be carefully trained to sense resistance.

When giving straightforward mouth-to-mouth resuscitation, however, the presence of an obstruction is more easily sensed. Resistance to air flow is immediately apparent to anyone attempting to blow into the mouth of a victim.

Accordingly, a system whereby mouth-to-mouth resuscitation could be applied, while at the same time applying supplemental free oxygen or gas mixture would be highly advantageous both from the viewpoint of initial cost and also from the viewpoint of operator sensitivity.

When gases are administered in other situations, and even self-administered, for example, for pain relief, anaesthetic purposes, or for simply recovering from smoke inhalation or the like, the existing systems currently in use provide a simple form of "demand" valve, which is connected to a pressurized source of gas. Such a demand valve incorporates an on/off valve controlling the supply of gas, and a flexible diaphragm, which senses the inhalation effort of the victim, and operates the on/off valve so that gas is supplied during inhalation. As soon as the victim exhales, the diaphragm moves in the reverse direction, and the on/off switch closes, and gas supply is halted.

Such demand valves are in wide usage.

There are, however, certain disadvantages associated with their use. If supply of the gas under pressure becomes exhausted, or if the supply tube is blocked, or bent, then the victim will be unable to breathe through the mask. If he is conscious he will, of course, immediately remove the mask. If, however, he is unconscious he may suffocate.

Demand valves of this kind may also be used for emergency administration of gases by medical personnel. Again, the assistant must be alert at all times to the possibility of blockage in the gas supply, so that he may immediately remove the mask in the event of failure.

Clearly, therefore, it is desirable to incorporate in such a demand valve an additional valving system whereby the victim or patient may be enabled to breathe atmospheric air, in the event of failure of the gas supply to the demand valve.

BRIEF SUMMARY OF THE INVENTION

The invention is directed to overcoming these various different problems, by providing a multi-function valve for the administration of gases comprising wall means defining a valve chamber having a gas administration opening, for delivery of gases to a patient, connectible with a suitable gas administration attachment, a pressurised gas inlet in the wall means, an inlet valve for said gas inlet, operating arm means associated with said inlet valve for operating arm said inlet valve, said operating means extending into the interior of said chamber, a wall portion of said chamber having resuscitation fluid inlet means, connectible to a resuscitation inlet supply a diaphram in said chamber, dividing the same into upstream and downstream chamber portions, with said resuscitation inlet means on one side of said diaphragm, and said gas administration opening and said gas supply inlet on the opposite side of said diaphragm, and contact means on said diaphragm movable into and out of contact with said valve operating means, and fluid flow opening means in said diaphragm, for fluid flow from one side of said chamber to the other.

More particularly, the invention provides such a multi-function valve wherein the diaphragm incorporates a central rigid contact member for contacting said valve operating member, and an annular flexible portion, permitting said diaphragm to move toward and away from said operating member.

More particularly, the invention comprises a valve having the foregoing advantages wherein the fluid flow opening through the diaphragm is dimensioned so as to cause said diaphragm to flex, in response to a moderate inhalation effort by the victim, while being sufficient to permit flow of air therethrough in response to a more vigorous inhalation effort by the victim.

More particularly, the invention comprises a valve having the foregoing advantages wherein such fluid flow opening in such diaphragm is dimensioned so as to permit resuscitation by mouth-to-mouth or manual means, by supply of fluid from said resuscitation inlet means and then through said fluid flow opening.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described preferred embodiments of the invention.

IN THE DRAWINGS

Figure 1:
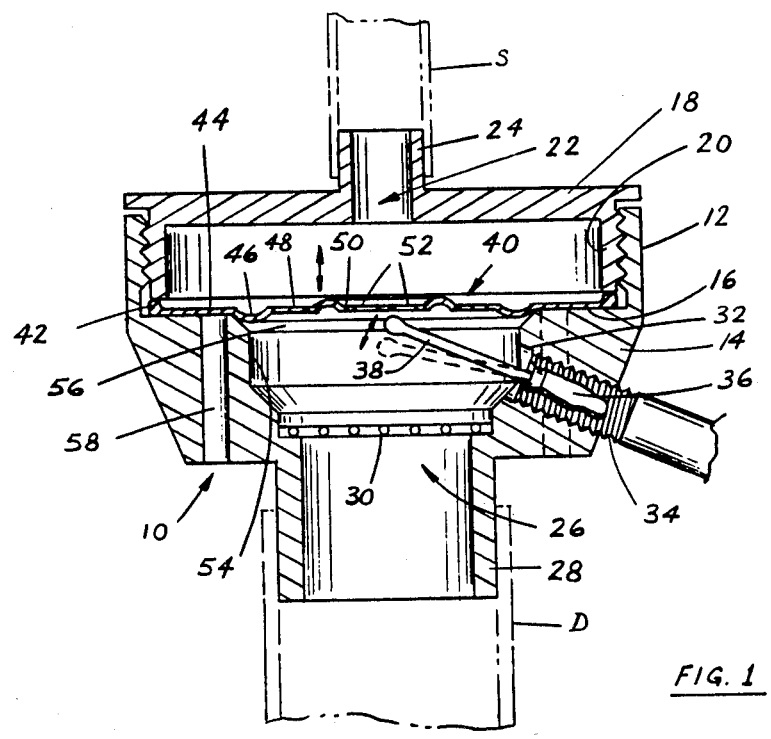
FIG. 1 is a section through a multi-function valve according to the invention, showing the diaphragm in its normal at rest position.
Figure 2:
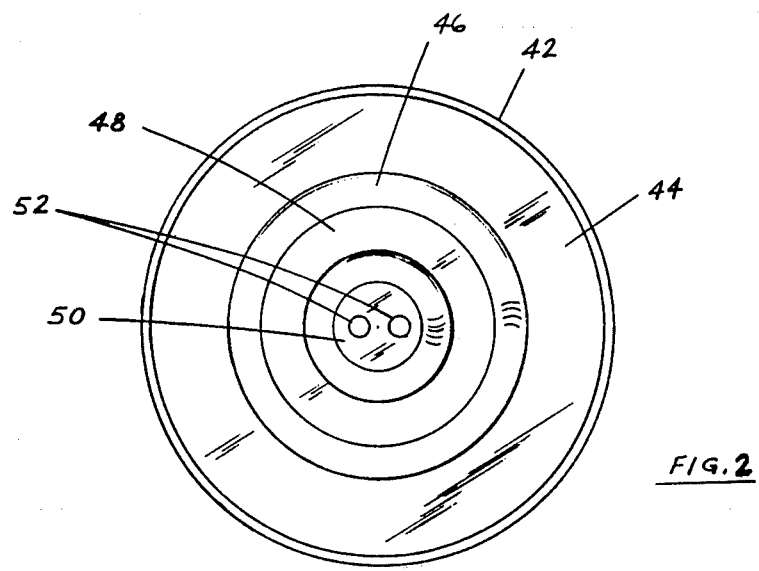
FIG. 2 is a top plan view of the diaphragm.
Figure 3:
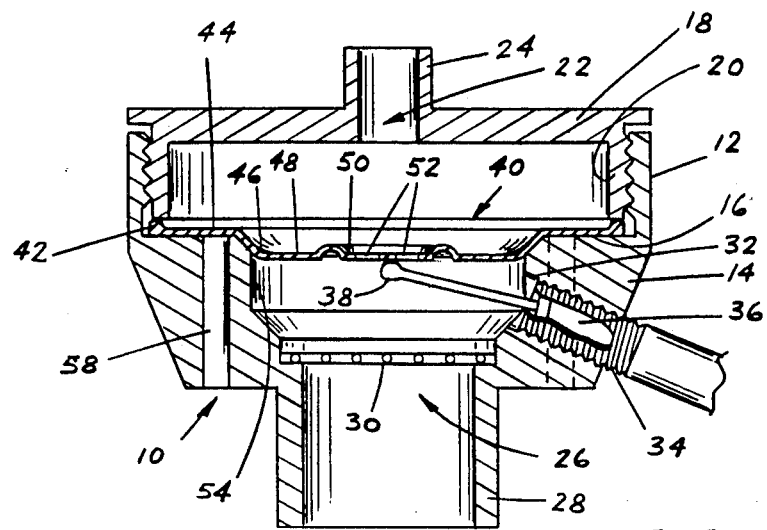
FIG. 3 is a partial section corresonding to FIG. 1, but showing the diaphragm in its inhalation or resuscitation position, and, FIG. 4 is a partial section corresponding to FIG. 3, showing the diaphragm in its exhalation position.
Figure 4:
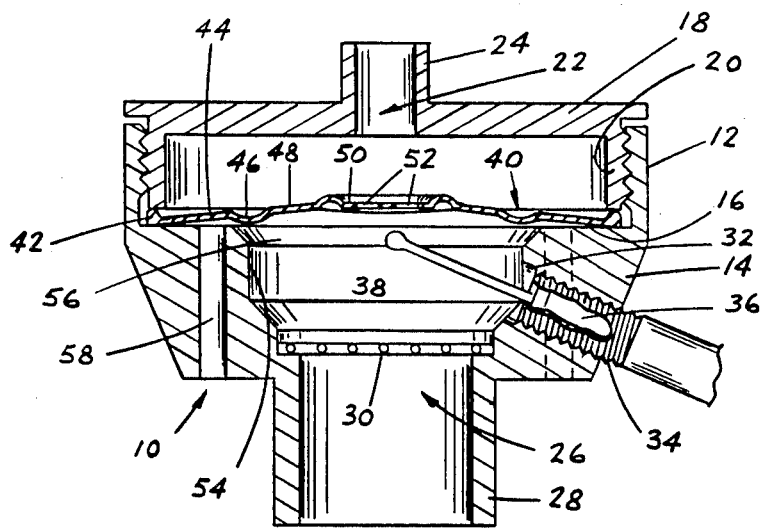

Referring first of all to FIG. 1, it will be seen that the invention generally comprises a multi-function valve having a generally cylindrical shape in this embodiment, the section being taken down the central axis along the diameter of such cylindrical shape.

It will, however, be appreciated that the invention is not solely restricted to such a shape, the shape being illustrated merely being one which can be most conveniently and economically formed in various fabricating techniques.

Referring now to FIG. 1, it will be seen that the invention is illustrated there in the particular form of a generally circular shaped structure, having upper and lower ends and a hollow interior, which will be described in more detail below.

It will, however, be appreciated that the invention is not restricted to such shape, but that it may be constructed in other shapes and forms, without well defined upper and lower ends, and may be constructed of a variety of materials such as machined metals, castings, thermoplastics and the like.

As illustrated in this embodiment, the valve chamber which is indicated generally as 10 comprises a generally annular or cylindrical shaped sidewall 12, and a frusto-conical wall portion 14. A generally annular ledge portion 16 extends inwardly into the interior of chamber 10, at approximately the level of the transition between wall portion 12 and wall portion 14, and the wall portion 14 is of substantially greater thickness than the wall portion 12.

The upper end of the cylindrical wall portion 12 is open, and is closed by means of a closure plate member 18, having a downwardly dependent skirt 20, extending downwardly within wall portion 12. A resuscitation fluid inlet opening 22 is located centrally of member 18, and has a typical frictional coupling 24 extending upwardly. Coupling 24 is typically sized to make a friction fit with the resuscitation mouthpiece, or any other form of resuscitation gas supply, indicated in phantom as S, the details of which are omitted for the sake of clarity.

At the lower end of wall portion 14, there is provided a gas administration opening 26, connecting with a suitable gas administration coupling 28. Coupling 28 is of a standard shape, designed to make a good friction fit with a typical gas administration device such as a face mask, or other breathing device such as a tube or the like, indicated generally as D. Typically, a wire or plastic mesh screen 30 will be located across outlet 26 to prevent passage of solid material in either direction.

A pressurized gas inlet opening 32 extends through wall 14, being located at an angle relative to the central axis of the chamber 10. A pressurised gas conduit 34 is threadedly engaged within suitable threaded means in opening 32.

The supply of pressurized gas is controlled by any suitable on/off control valve indicated as 36, of any suitable type such as is well known in the art. The valve member 36 will be secured typically by threaded means within the interior of the pressurised gas supply conduit 34.

Valve 36 will typically be operated by an operating arm 38. Arm 38 may be swung downwardly into the position shown in phantom, so as to allow flow of pressurized gas, and upon release of arm 38, it will spring back upwardly into the solid line position, thereby closing off supply of gas.

In order to cause operation of the arm 38, in response to an inspiratory effort by a patient or victim, a flexible diaphragm 40 is provided within chamber 10. Diaphragm 40 comprises an outer annular sealing rim 42, an outer flexible portion 44, an intermediate annular semicircular channel portion 46, and an inner flexible portion 48. A central rigid contact disk 50 is connected to the inner extremity of flexible portion 48, and has gas passageway means, which in this case comprise a pair of openings 54 extending therethrough.

The rigid contact member 50 is of a shallow saucer-like shape in section, and is adapted to extend downwardly into contact with the tip of arm 48.

The interior of wall portion 14 is machined out to define a reduced diameter cavity wall 54, the lower of which communicates with opening 26. At the upper end of cavity will 54, there is machined an angled valve seat 56. Valve seat 56 is intended to make sealing engagement with the annular channel portion 46 of diaphragm 40.

In order to provide a passageway for exhaled gases, a plurality of conduit drillings 58 are formed through the body of wall portion 14, and the upper ends of passageways 58 are normally closed off by the outer flexible portion 44 of diaphragm 40.

Various different modes of operation are possible with the valve according to the invention.

A. DEMAND VALVE

When in use as a simple demand valve, gases are normally being self-administered, or may administered in circumstances where a resuscitation treatment is impossible for example, in the case of an accident victim or the like.

In this case, the resuscitation valve supply S would not, of course, be connected to the coupling 24. In this type of operation, a breathing mask device will be represented as D, connected to coupling 28. The gas under pressure, typically oxygen, will be supplied through pressure gas supply conduit 34.

In these circumstances it is assumed that the victim is making a breathing effort, although this may or may not be a reduced effort depending upon the condition of the victim. In this case, the victim makes an inspiratory effort. This produces a reduced pressure in the cavity wall portion 54 of chamber 10. Diaphragm 40, through its flexible portion 48, will flex downwardly in an attempt to equalize this pressure. Contact member 50 will then contact the tip of arm 38 and depress it downwardly as shown in phantom. This will open up valve 36, thereby allowing supply of pressurized gas to flow into the cavity portion 54, and into the lungs of the victim.

When the victim exhales, the pressure in cavity 54 becomes momentarily positive. This will immediately cause diaphragm 40 to rise, thereby releasing arm 38 and shutting off valve 36. At the same time, the flexible portion 34 of diaphragm 48, due to the positive pressure, will lift off drillings 58, thereby allowing the exhaled air and gas to pass outwardly.

In the event of malfunction in the supply of pressurized gas, if this were a typical prior art demand valve, there would then be no gas supply within cavity 54 for the patient or victim to breathe.

However, in the case of the present embodiment, where the pressurized gas supply failed either through exhaustion, or through a kink in the pipe, for example, then the patient can inhale fresh air directly through gas passageways 52 in the contact portion 50. It will, of course, be understood that the gas passageways 52 will be of such a size and shape that they will permit air to flow into the cavity portion 54 in the lower region of the chamber 10 where the patient inhales, but are not so large that they will overcome the tendency of the diaphragm 40 to move downwardly in response to negative pressure produced by such an inhalation.

In practice, the sizing and shaping of such openings 52 can readily be arrived at by experimentation.

In this first mode of operation, it will thus be appreciated that a patient or victim may use the invention as a simple demand valve, for a variety of different treatment situations, with or without the assistance of a medical aid. In particular, where a medical aid is not present, or where he fails to notice the failure in the gas supply, the patient will be able to continue breathing, until the condition is rectified.

B. RESUSCITATION MODE

In this mode of operation, some form of resuscitation gas supply indicated generally as S will be connected to the upper coupling 24, and a typical mask device or other gas administration attachment D will be connected as before to coupling 28.

In this case it is assumed that the patient is temporarily unable to breathe, or is breathing only with great difficulty.

In this case, after the medical assistant makes the usual examination, of the mouth and air way and general condition of the victim, the gas administration device D is placed over the mouth, or down the throat of the victim. The medical assistant will place his mouth over the mouthpiece of the resuscitation supply S, and will then apply a resuscitation exhalation into the supply device S. This will then flow through opening 22 into the upper cylindrical portion of chamber 12 within skirt 20, and wall 12. This will cause a slight positive pressure in the upper chamber portion. This will cause the diaphragm 40 to be depressed downwardly, thereby contacting arm 38, and opening valve 36.

As the medical assistant continues to blow into the supply device S, exhaled air from the assistant will flow through the opening 22, and through the openings 52 in the diaphragm 40, and out through the opening 26 into the breathing passages of the victim. However, unlike conventional resuscitation, this resuscitation air will be enriched by the supply of pressurized gas such as oxygen, or oxygen and other gases, flowing inwardly to the lower chamber portion through the gas supply 34.

As soon as the medical assistant stops the resuscitation breathing effort, the natural resilience of the lungs of the patient will cause exhalation from the patient. This will reverse the pressures within the chamber 10, so that the pressure in the upper portion of the chamber 10 goes to atmospheric, and the pressure in the lower portion of the chamber 10 goes positive. This, then, will cause the diaphragm 40 to flex upwardly, thereby shutting off the valve 36, and at the same time opening up the exhalation passageways 10 to permit outflow of exhaled air.

The two openings 52 in the diaphragm have a relatively small open area, and the plurality of conduits 58 have a relatively larger open area. Consequently the air exhaled by the patient does not return through the openings 52 and into the mouth of the medical assistant, but merely escapes to the atmosphere through the openings 58.

The medical assistant is thus avoiding any direct contact with the person or exhaled breath of the victim or patient, and is thus free from any danger of infection.

In the event that the airway of the patient is blocked, the medical assistant will immediately sense the presence of the blockage. He will immediately sense that his breathing effort into the device S is being resisted by some abnormality, and will then discontinue resuscitation while he again checks the patient's airway for an obstruction.

C. MANUAL BAG RESUSCITATION

In this case, the device S represents a manual air bag such as is used for resuscitation by more skilled and experienced medical assistants. In this case, the resuscitation effort is applied by squeezing the bag, thereby causing flow of fresh air from the bag, which may in some cases be further enriched with other gases, such gases flowing through the opening 22 into the upper portion of chamber 10.

Resuscitation and exhalation then continue as before.

In this case, however, if there is an obstruction, the medical assistant will require considerably more experience to detect it, due to increased resistance in the bag itself.

The foregoing is a description of a preferred embodiment of the invention which is given here by way of example only. The invention is not to be taken as limited to any of the specific features as described, but comprehends all such variations thereof as come within the scope of the appended claims.

What is claimed is:

1. A multi-function valve for the administration of gases comprising:

housing means defining a valve chamber therein and having a pressurized gas inlet therein for delivery of gases to said chamber adapted for connection with a pressurized gas source, a gas administration opening therein for delivery of gases from said chamber to a patient adapted for connection with a suitable gas administration attachment and a resuscitation gas inlet therein for delivery of resuscitation gas to said chamber adapted for connection with a resuscitation gas source;

a diaphragm mounted across said chamber and sealed to said housing means to divide said chamber into upstream and downstream chamber portions, said resuscitation gas inlet positioned on the upstream side of said diaphragm and said pressurized gas inlet and said gas administration opening positioned on the downstream side of said diaphragm, said diaphragm being movable in response to pressure differences thereacross, said diaphragm having a central contact portion movable in unison therewith;

inlet valve means connected to said pressurized gas inlet for controlling flow of pressurized gas into said chamber;

valve operating arm means connected to said inlet valve means and extending therefrom into abutment with the contact portion of said diaphragm for operating said inlet valve means in response to movement of said diaphragm;

fluid flow opening means in said diaphragm for permitting fluid flow from said upstream side of said diaphragm to the downstream side thereof; and exhalation means associated with said housing means and positoned on the downstream side of said diaphragm for discharge of exhaled gas from the patient to the atmosphere.

2. A multi-function valve as claimed in claim 1 wherein said fluid flow opening means in said diaphragm are dimensioned so as to cause said diaphragm to flex in response to a moderate inhalation effort by the patient, while being sufficient to permit flow of fluid therethrough in response to a more vigorous inhalation effort by the patient.

3. A multi-function valve as claimed in claim 2 wherein said fluid flow opening means in said diaphragm are dimensioned so as to permit resuscitation by the resuscitation gas source which supplies resuscitation gas through said resuscitation gas inlet and then through the fluid flow opening means in said diaphragm.

4. A multi-function valve as claimed in claim 1 wherein said housing means further defines an annular valve seat within said downstream chamber portion adjacent to said diaphragm, and said diaphragm includes a generally annular valve seat contacting portion formed around said central contact portion and dimensioned to inter-engage with said valve seat.

5. A multi-function valve as claimed in claim 4 wherein said diaphragm includes an outer annular planar portion located around said annular valve seat contacting portion.

6. A multi-function valve as claimed in claim 5, wherein said diaphragm includes a perimeter rim portion of thicker longitudinal section than the remainder of said diaphragm.

7. A multi-function valve as claimed in claim 4 wherein said housing means defining said chamber comprises an upper wall portion of generally cylindrical shape having an open lower end and a lower wall portion of generally inverted frusto-conical shape having an open base extending from said lower open end and coaxial therewith, said lower wall portion being thicker in cross-section than said upper wall portion and a generally planar annular surface defined by the intersection of said upper wall portion and said lower wall portion froming a mounting surface for said diaphragm and defining said valve seat.

8. A multi-function valve as claimed in claim 7 wherein said exhalation means comprises open ended passageways extending upwardly through said lower wall portion and opening at one end at said generally planar annular surface and at the other end to the atmosphere, whereby said openings are covered by said diaphragm except when said diaphragm flexes in response to exhalation by the patient.

9. A multi-function valve as claimed in claim 8 wherein said upper wall portion further includes an upper open end opposite said lower open end, a closure member of generally annular planar configuration, and fastening means for fastening said closure member to the upper open end of said upper wall portion, said resuscitation gas inlet being located in said closure member.

10. A multi-function valve as claimed in claim 9 wherein said inlet valve means is received in said pressurized gas inlet for controlling flow of pressurized gas.

11. A multi-function valve as claimed in claim 10 wherein said fastening means includes a generally cylindrical skirt portion on said closure member depending therefrom and adapted to extend within said upper wall portion of said chamber, and complimentary fastening threads on said skirt portion and said upper wall whereby said skirt portion and said upper wall portion are threadedly fastened together, said skirt portion being adapted to engage the perimeter of said diaphragm and hold and seal said diaphragm in position against said generally planar annular surface.

12. A multi-function valve as claimed in claim 1 wherein said central contact portion comprises an annular rigid member for abutting said valve operating arm means and said diaphragm further includes an annular flexible portion around said annular rigid member permitting said diaphragm to move in response to pressure differences thereacross.

* * * * *